United States Patent [19]

Damani et al.

[11] Patent Number: 5,560,921
[45] Date of Patent: Oct. 1, 1996

[54] CHEWABLE DECONGESTANT COMPOSITIONS

[75] Inventors: Nalinkant C. Damani, Cincinnati, Ohio; Rita Vienhues, Weybridge, Great Britain

[73] Assignee: The Procter & Gamble Company, Cincinnati, Ohio

[21] Appl. No.: 347,305

[22] PCT Filed: May 18, 1993

[86] PCT No.: PCT/US93/04688

§ 371 Date: Apr. 28, 1995

§ 102(e) Date: Apr. 28, 1995

[87] PCT Pub. No.: WO93/24111

PCT Pub. Date: Dec. 9, 1993

[30] Foreign Application Priority Data

Jun. 1, 1992 [EP] European Pat. Off. ............. 92304982

[51] Int. Cl.$^6$ .............. A61K 9/48; A61K 9/68; A61K 9/20; A61K 47/12
[52] U.S. Cl. .......... 424/441; 424/440; 424/464; 424/468; 424/470; 514/784
[58] Field of Search ............................... 424/440, 441, 424/464, 468, 470; 514/784

[56] References Cited

U.S. PATENT DOCUMENTS

| 3,592,945 | 7/1971 | Engelking | 252/316 |
| 4,940,588 | 7/1990 | Sparks et al. | 424/490 |
| 4,952,402 | 9/1990 | Sparks et al. | 424/441 |
| 4,971,791 | 11/1990 | Tsau et al. | 424/441 |

OTHER PUBLICATIONS

Chemical Abstracts, 108(18), 156496a, 1988.
Chemical Abstracts 113(26): 237719f, 1990.
Chemical Abstracts 117(6): 55827q, 1991.
Chemical Abstracts 118(16): 154570c, 1993.
Biosis Abstract 90: 335746, BA 90, 43765, 1990.

*Primary Examiner*—Carlos Azpuru
*Attorney, Agent, or Firm*—Douglas C. Mohl; Jacobus C. Rasser; David K. Dabbiere

[57] ABSTRACT

The present invention relates to immediate release compositions comprising a pre-complex comprising a polymeric polycarboxylate and an aminophenylalkanol vasoconstrictor in a solid chewable matrix of pharmaceutically-acceptable carrier ingredients wherein the aminophenylalkanol vasoconstrictor and polymeric polycarboxylate are in a weight ratio of from about 5:1 to about 1:10 and wherein the pre-complex is dissociable at a pH of from about 4.5 to about 6.8, releasing the aminophenylalkanol vasoconstrictor.

17 Claims, No Drawings

CHEWABLE DECONGESTANT COMPOSITIONS

FIELD OF THE INVENTION

This invention relates to an oral decongestant composition. In particular, it relates to an oral decongestant composition in solid, chewable form having improved absorption characteristics and higher patient compliance. In addition, the invention relates to methods for preparing such a composition.

BACKGROUND OF THE INVENTION

Pharmaceuticals for oral ingestion can take many different forms, such as liquids, emulsions, suspensions, aerosol sprays, solid capsules or tablets. Many pharmaceutical compositions including oral decongestants contain unpalatable ingredients and are therefore marketed in the form of liquids and sprays. Pharmaceutical compositions in the form of tablets or capsules which are intended to be swallowed whole are also widely marketed. Taste-masking of the active ingredients contained in such products can be effected by covering the tablet with a thin and quickly dissolving coating, for example, using a gelatin outer shell in order to retain the active ingredient until the tablet has been swallowed. Alternatively, the tablet can be compressed sufficiently so that it stays intact for the short time that it is in the mouth.

It would be desirable to provide solid, chewable and lozenge forms of dosage. These are preferred by people who do not like or have difficulty swallowing tablets or capsules, particularly children and older people. Furthermore, solid, chewable tablets have higher patient compliance than liquids since they are more convenient to carry around. Frequently the bitter taste of pharmaceutically-active ingredients has been masked so that such drugs can be adapted into acceptable-tasting chewable and lozenge forms.

The concept of providing pharmaceuticals in solid, chewable form has been disclosed in EP-A-0,459,695, where the chewable tablets are made from coated granules of medicament. The coating on these granules comprises a blend of cellulose acetate and/or cellulose acetate butyrate and hydroxypropyl cellulose and provides taste-masking of the active ingredient and sustained-release of the medicament.

EP-A-0,284,408 also discloses a chewable tablet comprising a controlled-release drug in which granules are coated with a polymer or copolymer of alkyl esters of acrylic and methacrylic acids and ethyl cellulose.

GB-A-2,166,651 relates to a controlled-release powder consisting of discrete microparticles for use in edible pharmaceutical compositions. The particles contain an active ingredient and optionally an excipient in intimate admixture with at least one non-toxic polymer. Each of the particles are in the form of a micromatrix with active ingredient and the excipient, if present, uniformly distributed throughout the matrix. These particles have an average size of between 0.1 and 125 µm.

EP-A-0,212,641 discloses a porous drug-polymer matrix with an amino- or amido- containing drug such as dimenhydrinate or salt thereof as the active ingredient and a pharmaceutically-acceptable copolymer having a plurality of carboxylic acid and ester groups wherein the matrix dissociates in a media having a pH of less than 4, thereby releasing the active ingredient into the acidic media of the stomach.

U.S. Pat. No. 3,629,392 discloses an aqueous latex of a polymer having acidic and/or basic groups in contact with a drug also having basic and/or acidic groups. The water is then removed and the product formulated into a suitable dosage form. An aqueous "latex" herein means an aqueous dispersion of colloidal or near colloidal particles.

U.S. Pat. No. 3,515,781 discloses a capsule containing menthol, thymol and an oral decongestant and which dissolves in the mouth to release these substances for the alleviation of the symptoms of nasal congestion.

While there has been a number of proposals in the art for providing oral decongestants and other orally-ingestible pharmaceuticals in chewable, sustained- or controlled-release tablet form, there has apparently been no disclosure of an oral decongestant composition in solid, chewable dosage form which allows for fast release of the decongestant, together with improved taste and consumer acceptability.

Accordingly, the present invention provides a chewable oral decongestant composition having enhanced release characteristics combined with improved taste and consumer acceptability.

SUMMARY OF THE INVENTION

According to one aspect of the present invention, there is provided an oral decongestant composition comprising an aminophenylalkanol vasoconstrictor in a solid chewable matrix of pharmaceutically-acceptable carrier ingredients, and wherein the aminophenylalkanol vasoconstrictor is present in the form of a pre-complex with a polymeric polycarboxylate, the pre-complex comprising the aminophenylalkanol vasoconstrictor and polymeric polycarboxylate in a weight ratio of from about 5:1 to about 1:10 and being dissociatable in aqueous media having a pH of between about 4.5 and about 6.8, with release of the aminophenylalkanol vasoconstrictor.

The oral decongestant composition of the present invention can be formed by dissolving the aminophenylalkanol vasoconstrictor with the pharmaceutically-acceptable polymeric polycarboxylate in an organic solvent or aqueous organic solvent mixture and thereafter removing the solvent to form the aminophenylalkanol vasoconstrictor pre-complex. Thereafter the pre-complex and pharmaceutically-acceptable carrier ingredients are admixed and optionally tableted to yield the oral decongestant composition in solid chewable form. The oral decongestant composition of the present invention can also be formed by a method wherein the aminophenylalkanol vasoconstrictor is in salt form, and wherein the method comprises reducing the particle size of the aminophenylalkanol vasoconstrictor to less than about 300 µm, admixing the pharmaceutically-acceptable polymeric polycarboxylate and water to form a slurry, followed by adding a stoichiometric amount of sodium hydroxide solution to the slurry with increased mixing and thereafter drying the aminophenylalkanol vasoconstrictor pre-complex. Again the pre-complex and pharmaceutically-acceptable carrier ingredients are admixed and optionally tableted to give the oral decongestant in solid chewable tablet form. The oral decongestant of the present invention is chewable to initiate release of the active ingredient in the mouth and subsequently in the stomach/intestine.

DETAILED DESCRIPTION OF THE INVENTION

In accordance with the present invention a solid, chewable tablet is formed comprising an aminophenyl $C_2$–$C_3$ alkanol vasoconstrictor as an oral decongestant and wherein the aminophenyl $C_2$–$C_3$ alkanol vasoconstrictor is in the form of a pre-complex with the polymeric polycarboxylate. The polymeric polycarboxylate is chosen such that the pre-complex is dissociatable in water or aqueous media at a pH at least in the range from about 4.5 to about 6.8, with release of the aminophenyl $C_2$–$C_3$ alkanol vasoconstrictor. The aminophenylpropanol vasoconstrictor can be selected from 2-amino-1-phenyl-1-$C_2$–$C_3$ alkanols, N-$C_1$–$C_4$ alkyl derivatives, salts and mixtures thereof. Optionally, the phenyl moiety of the 2-amino-1-phenyl-1-$C_2$–$C_3$ alkanol can be substituted by one or more hydroxy groups. In preferred embodiments of the invention the aminophenyl $C_2$–$C_3$ alkanol vasoconstrictor is selected from pseudoephedrine and phenylpropanolamine. Other suitable aminophenyl $C_2$–$C_3$ alkanols include phenylephrine and phenylethanolamine. The pharmaceutically-acceptable copolymer component of the composition of the present invention is preferably a polymeric polycarboxylate comprising methacrylic acid and methyl methacrylate. Such polymeric polycarboxylates are capable of interacting with the aminophenyl $C_2$–$C_3$ alkanol vasoconstrictor to bring about effective taste-masking of the bitter tasting active material. Preferred polycarboxylates for use in the present invention are commercially available under the trade name Eudragit-L-100 (trade mark of Röhm Pharma).

The aminophenyl $C_2$–$C_3$ alkanol vasoconstrictor has an amine group which is capable of interacting with the carboxylic acid groups of the copolymer, to form a pre-complex by, for example, hydrogen bonding, salt formation or ion-pair formation.

The pre-complex can be prepared by dissolving aminophenyl $C_2$–$C_3$ alkanol vasoconstrictor with the pharmaceutically-acceptable copolymer in an alcoholic or aqueous alcoholic solution comprising from 1 to 4 carbon atoms, for example, ethanol. The solvent can be removed by any one of a number of methods including evaporation under vacuum, spray drying, tray drying, drum or belt film drying. The preferred method of solvent removal in the present invention is by evaporation under vacuum at elevated temperatures, preferably at least about 30° C.

An additional method for preparing the pre-complex comprises reducing the particle size of the aminophenyl $C_2$–$C_3$ alkanol vasoconstrictor to less than about 300 μm, the aminophenyl $C_2$–$C_3$ alkanol vasoconstrictor being in salt form, admixing the pharmaceutically-acceptable polymeric polycarboxylate and water to form a slurry, followed by adding a stoichiometric amount of sodium hydroxide solution to the slurry with increased mixing and thereafter drying the aminophenylalkanol vasoconstrictor pre-complex. A number of methods can be used herein for drying the pre-complex selected from evaporation under vacuum, spray drying, tray drying, drum or belt film drying. The preferred method of drying the pre-complex prepared by this method is by evaporation under vacuum at elevated temperatures, preferably at least about 60° C.

The oral decongestant composition of the present invention preferably comprises from about 1% to about 15%, more preferably from about 2% to about 10%, by weight thereof of aminophenyl $C_2$–$C_3$ alkanol vasoconstrictor and from about 1% to about 30%, more preferably from about 5% to about 20% by weight thereof of the copolymer. In preferred embodiments the monomer ratio of methacrylic acid to methyl methacrylate is from about 3:1 to about 2:3.

The composition of the invention comprises the aminophenyl $C_2$–$C_3$ alkanol vasoconstrictor pre-complex within a solid chewable matrix of pharmaceutically-acceptable carrier ingredients. Suitable carrier ingredients can be selected from sugars, sugar substitutes, and mixtures thereof. The sugars or sugar substitutes can be selected from Talin, sucrose, glucose, fructose, high fructose corn syrup, invert sugar, mannitol, sorbitol and mixtures thereof. In preferred embodiments, the matrix of carrier ingredients and the aminophenyl $C_2$–$C_3$ alkanol vasoconstrictor pre-complex are in a weight ratio in the range of from about 1:1 to about 50:1, preferably from about 1:10 to about 30:1. The matrix can additionally comprise conventional colouring agents, fillers and plasticizers, flavouring agents, colouring agents and/or artificial sweetening agents. Suitable artificial sweeteners can be selected from aspartame, cyclamate, saccharin, Acesulfame™ K and mixtures thereof.

Suitable flavouring agents include an aromatic flavouring agent selected from menthol, peppermint oil, camphor, eucalyptol, eucalyptus oil, preferably menthol. It is a feature of the invention that the addition of the aromatic flavouring agent in combination with the aminophenylpropanol vasoconstrictor pre-complex is especially valuable for providing improved decongestant release characteristics and patient compliance.

According to another aspect of the invention, there is provided an oral decongestant composition comprising an aromatic flavouring agent together with an aminophenyl $C_2$–$C_3$ alkanol vasoconstrictor in a solid chewable matrix of pharmaceutically-acceptable carrier ingredients, and wherein the aminophenyl $C_2$–$C_3$ alkanol vasoconstrictor is present in the form of a pre-complex with a polymeric polycarboxylate, the pre-complex comprising the aminophenyl $C_2$–$C_3$ alkanol vasoconstrictor and polymeric polycarboxylate in a weight ratio of from about 5:1 to about 1:10 and being dissociatable in a media having a pH in the range from about 4.5 to about 6.8, with release of the aminophenyl $C_2$–$C_3$ alkanol vasoconstrictor.

The compositions of the present invention can be provided in various forms, for example, solid chewable tablets, capsules and lozenges. The amount of the aminophenyl $C_2$–$C_3$ alkanol vasoconstrictor pre-complex present per unit dose of the final composition is from about 50 mg to about 500 mg, preferably from about 70 mg to about 250 mg. The amount of aminophenyl $C_2$–$C_3$ alkanol vasoconstrictor per unit dose of the final composition, on the other hand, is preferably from about 20 mg to about 250 mg, especially from about 40 mg to about 150 mg.

The present invention is illustrated by the following examples.

EXAMPLE 1

An oral decongestant composition of the invention is prepared as follows. 25 g of pseudoephedrine hydrochloride salt is dissolved in about 25 g water. A stoichiometric amount of a 10% sodium hydroxide solution is added to the solution to precipitate pseudoephedrine in the form of a slurry. 50 g of Eudragit-L-100 polymer is added to the slurry with mixing. About 25 g of ethanol is added to the mixture in order to solubilize the polymer and complete the drug-polymer interaction. The mixture is dried under vacuum at about 55° C. and is then granulated by passing it through a 177 μm sieve (mesh #80). The pseudoephedrins pre-complex thus prepared is then incorporated in a tablet-form oral decongestant composition as follows:

10 mg of aspartame and 10 mg of finely powdered menthol are mixed with 180 mg of the drug-polymer complex. 250 mg of mannitol and 25 mg of aspartame are added, followed by admixing of 515 mg of sorbitol. 10 mg of magnesium stearate is then added as a lubricant and the tablets are compressed at a pressure of 3 metric tons.

EXAMPLE 2

A second oral decongestant is prepared as follows:

50 g of pseudoephedrine hydrochloride is ground to give a particle size of less than about 300 μm and then mixed thoroughly with 100 g of Eudragit L-100. 120 ml of water is added with mixing to form a slurry. A stoichiometric amount of 10% sodium hydroxide solution is added to the slurry with increased mixing. The mixture is dried under vacuum at about 60° C. and is then passed through a 300 μm sieve to obtain the pseudoephedrine pre-complex in granulated form. The pseudoephedrine pre-complex is then incorporated in a tablet-form oral decongestant composition as follows:

200 mg of pseudoephedrine pre-complex is ground and passed through a 300 μm sieve. 10 mg each of aspartame and finely powdered menthol is then mixed with the pseudoephedrine pre-complex. 250 mg of mannitol is added along with 25 mg of aspartame, followed by admixing of 500 mg of sorbitol. Addition of 10 mg of magnesium stearate is followed by compression of the mixture at a pressure of 3 metric tons to form tablets.

The oral decongestants of Examples 1 and 2 demonstrate improved absorption characteristics together with higher patient compliance.

We claim:

1. An oral decongestant composition comprising an aminophenylalkanol vasoconstrictor in a solid chewable matrix of pharmaceutically-acceptable carrier ingredients, and wherein the aminophenylalkanol vasoconstrictor is present in the form of a pre-complex with a polymeric polycarboxylate consisting of methacrylic acid and methyl methacrylate, the pre-complex comprising the aminophenylalkanol vasoconstrictor and the polymeric polycarboxylate in a weight ratio of from about 5:1 to about 1:10 and being dissociable in aqueous media having a pH of between about 4.5 to about 6.8, with release of the aminophenylalkanol vasoconstrictor.

2. An oral decongestant composition according to claim 1 wherein the aminophenylalkanol vasoconstrictor is selected from the group consisting of 2-amino-1-phenyl-1-ethanols, 2-amino-1-phenyl-1-propanols, 2-methylamino-1-phenyl-1-alkanols, 2-ethylamino-1-phenyl-1-alkanols, 2-propylamino-1-phenyl-1-alkanols, 2-butylamino-1-phenyl-1-alkanols, pharmaceutically acceptable salts, and mixtures thereof.

3. An oral decongestant composition according to claim 2 wherein the aminophenylalkanol vasoconstrictor is selected from the group consisting of pseudoephedrine, phenylephrine or phenylpropanolamine and mixtures thereof.

4. An oral decongestant composition according to claim 1 which comprises:
   a) from about 1% to about 15% by weight of composition of the aminophenylalkanol vasoconstrictor, and
   b) from about 1% to about 30% by weight of composition of the polymeric polycarboxylate.

5. An oral decongestant composition according to claim 4 wherein the copolymer comprises methacrylic acid and methyl methacrylate in a monomer ratio of from about 3:1 to about 2:3.

6. An oral decongestant composition according to claim 1 wherein the matrix of carrier ingredients comprises one or more materials selected from the group consisting of sugars, sugar substitutes, and mixtures thereof.

7. An oral decongestant composition according to claim 6 wherein the sugar or sugar substitute is selected from the group consisting of Talin, sucrose, glucose, fructose, high fructose corn syrup, invert sugar, mannitol, sorbitol and mixtures thereof.

8. An oral decongestant composition according to claim 1 wherein the matrix of carrier ingredients additionally comprises one or more plasticizers, fillers, flavouring agents, colouring agents and/or artificial sweetening agents.

9. An oral decongestant composition according to claim 8 wherein the artificial sweetening agent is selected from the group consisting of aspartame, cyclamate, saccharin, acesulfame K and mixtures thereof.

10. An oral decongestant composition according to claim 8 in which the flavouring agent is an aromatic flavouring agent.

11. A method for producing the pre-complex of the oral decongestant composition according to claim 1 comprising dissolving the aminophenylalkanol vasoconstrictor with the pharmaceutically-acceptable polymeric polycarboxylate in an organic solvent or aqueous organic solvent mixture and thereafter removing the solvent to form the aminophenylalkanol vasoconstrictor pre-complex.

12. A method according to claim 11 wherein the solvent is removed under vacuum at a temperature of at least about 30° C.

13. A method according to claim 12 wherein the solvent is a lower alcohol comprising from 1 to 4 carbon atoms.

14. A method for producing the pre-complex of the oral decongestant composition according to claim 1 wherein the aminophenylalkanol vasoconstrictor is in salt form and wherein the method comprises reducing the particle size of the aminophenylalkanol vasoconstrictor to less than about 300 μm, admixing the pharmaceutically-acceptable polymeric polycarboxylate and water to form a slurry, followed by adding a stoichiometric amount of sodium hydroxide solution to the slurry with increased mixing and thereafter drying the aminophenylalkanol vasoconstrictor pre-complex.

15. A method according to claim 14 wherein the aminophenylalkanol vasoconstrictor pre-complex is dried under vacuum at a temperature of about 60° C.

16. An oral decongestant composition according to claim 2 wherein the phenyl moiety of the aminophenylalkanol contains at least one hydroxy group.

17. An oral decongestant composition according to claim 10 wherein the aromatic flavouring agent is menthol.

\* \* \* \* \*